(12) United States Patent
Robinson, Jr.

(10) Patent No.: US 6,476,622 B2
(45) Date of Patent: *Nov. 5, 2002

(54) METHODS AND APPARATUS FOR MEASURING ELECTRICAL CHANGES IN NEOPLASMS AND FOODBORNE PATHOGENS IN A LIQUID MEDIUM

(76) Inventor: William L. Robinson, Jr., One E. Chase St., Baltimore, MD (US) 21202

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/262,059

(22) Filed: Mar. 4, 1999

(65) Prior Publication Data

US 2002/0000814 A1 Jan. 3, 2002

(51) Int. Cl.[7] ............................................... G01R 27/08
(52) U.S. Cl. ............................................................ 324/692
(58) Field of Search ........................... 324/692, 71.5, 324/450, 427, 439; 426/232, 412, 523; 429/102, 104; 435/7.5, 289.1, 284.1, 287.1, 287.2, 287.8

(56) References Cited

U.S. PATENT DOCUMENTS 3,708,578 A * 1/1973 Das ............................ 424/141
3,781,659 A * 12/1973 Ur ............................. 324/30 R
5,483,166 A * 1/1996 Olsen .......................... 324/450
5,587,520 A * 12/1996 Rhodes ....................... 73/25.03

* cited by examiner

Primary Examiner—N. Le
Assistant Examiner—Etienne P LeRoux
(74) Attorney, Agent, or Firm—Peter Gibson

(57) ABSTRACT

Rapid determination of pathogen and neoplasm levels is associated with irradiation in the processing of meat in order to assure quality with regard to both desired pathogen levels and integrity of the meat minimizing the level of irradiation utilized. Rapid determination of pathogen and neoplasm level by sensitive measurement of the rate of change of electrical impedance through a sample tested in a conductivity cell is suggested. Use of ultrasonic aqueous bath of sufficient energy level to cause cavitation impingement of the exterior surfaces of the meat so immersed is also suggested. The use of ultrasound achieves accelerated natural depuration by stimulating the natural excretory processes of living shellfish and achieves microscopic cleansing of the exterior of shellfish alive or dead. Said irradiated sample is analyzed for metabolic activity of foodborne contaminants and displayed as a two or three dimensional model. Genetic variations of suspected contaminants maybe confirmed using DNA Target sequencing techniques.

10 Claims, 7 Drawing Sheets

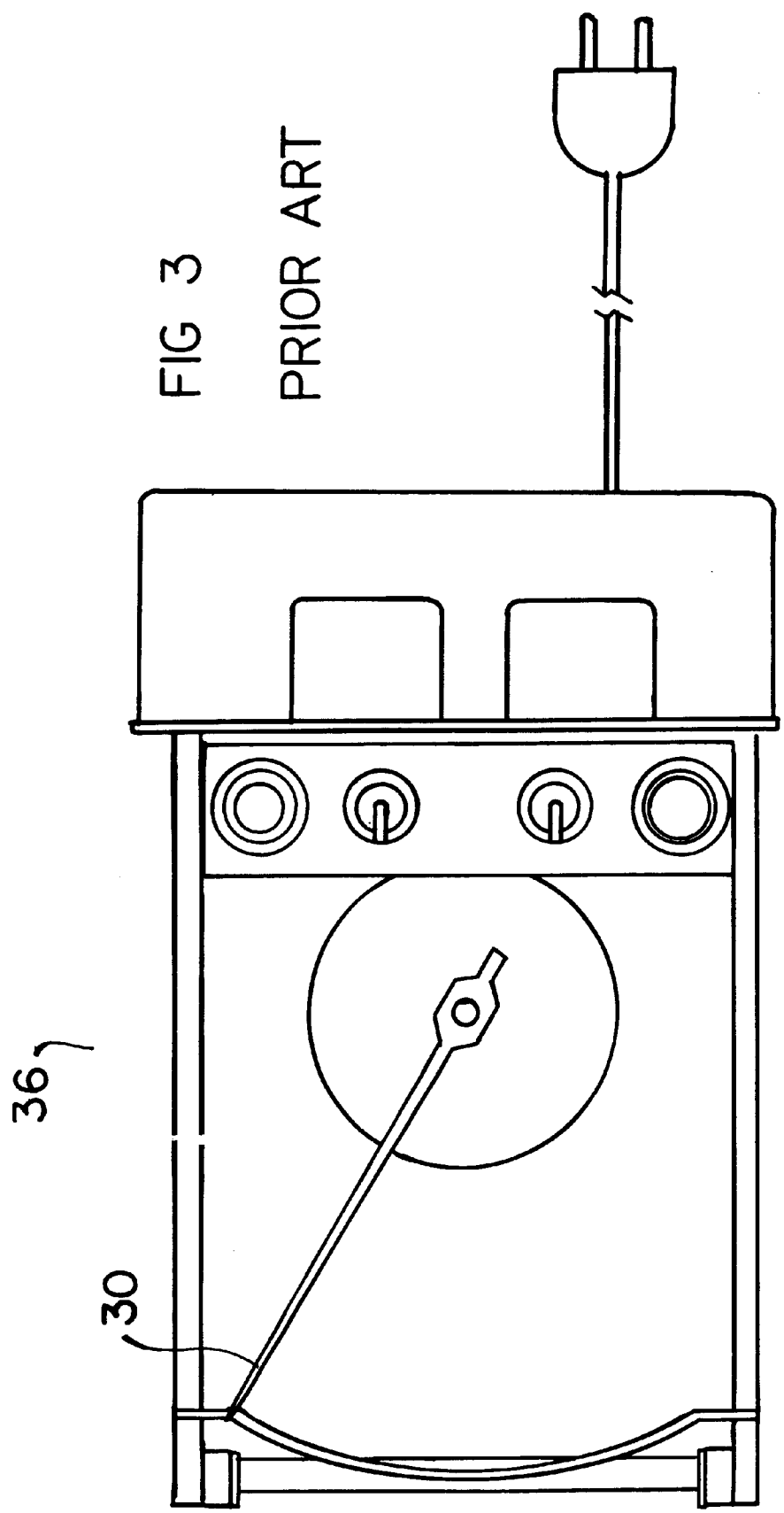

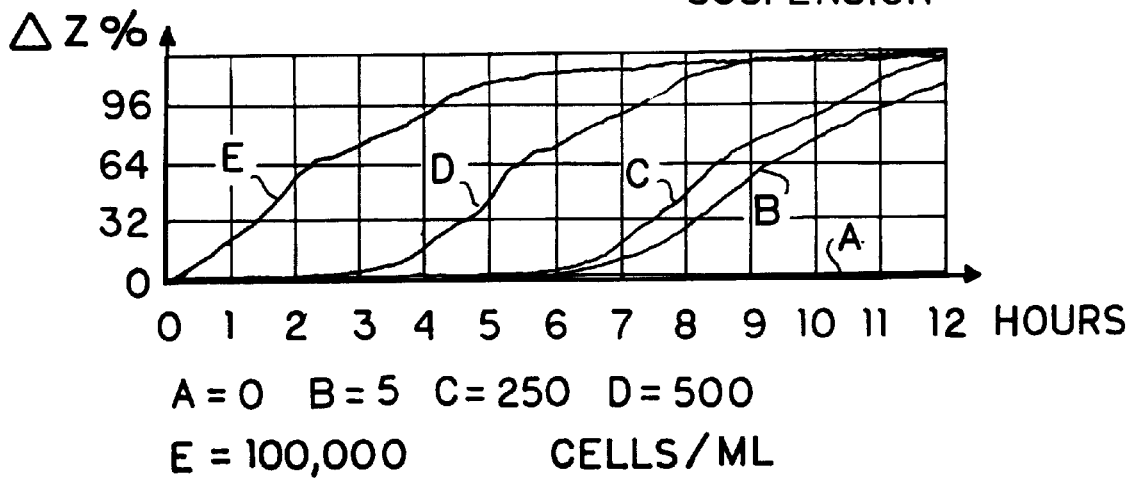
FIG. 5A
FIG. 5B
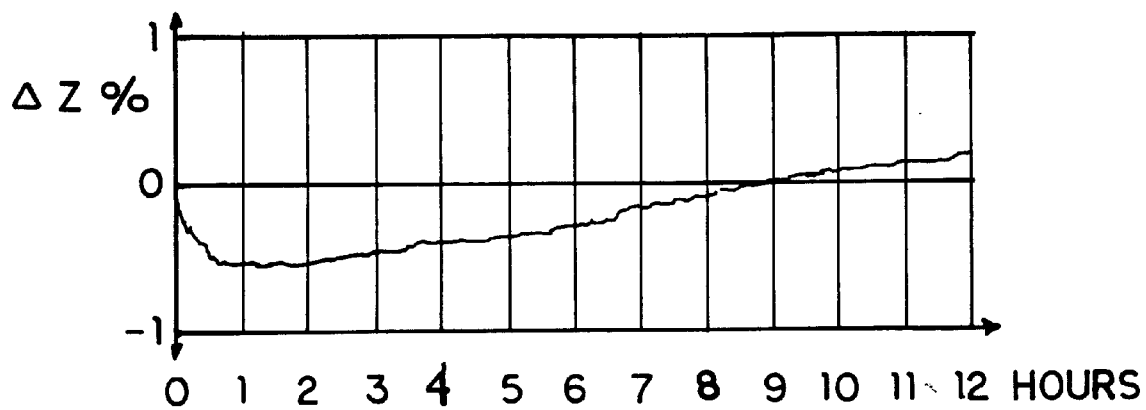

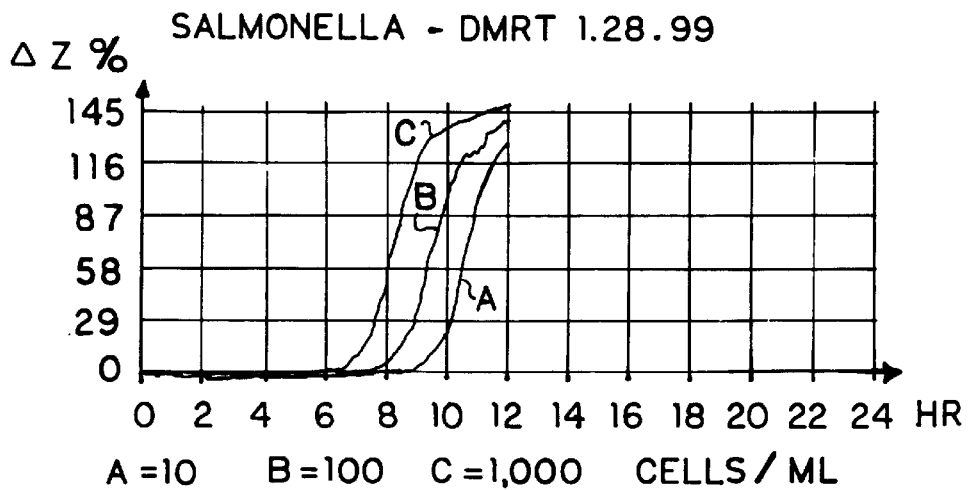
FIG. 6
FIG. 7
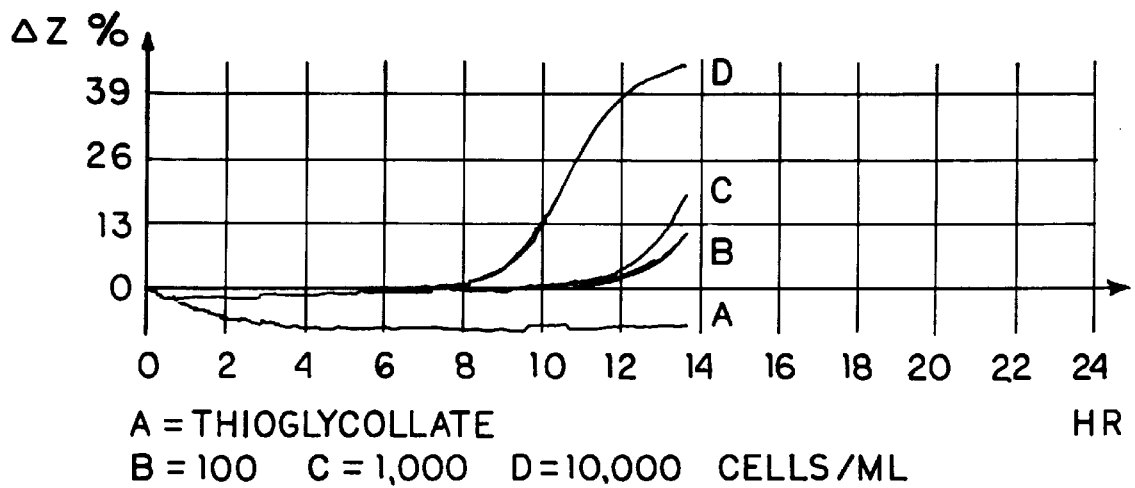

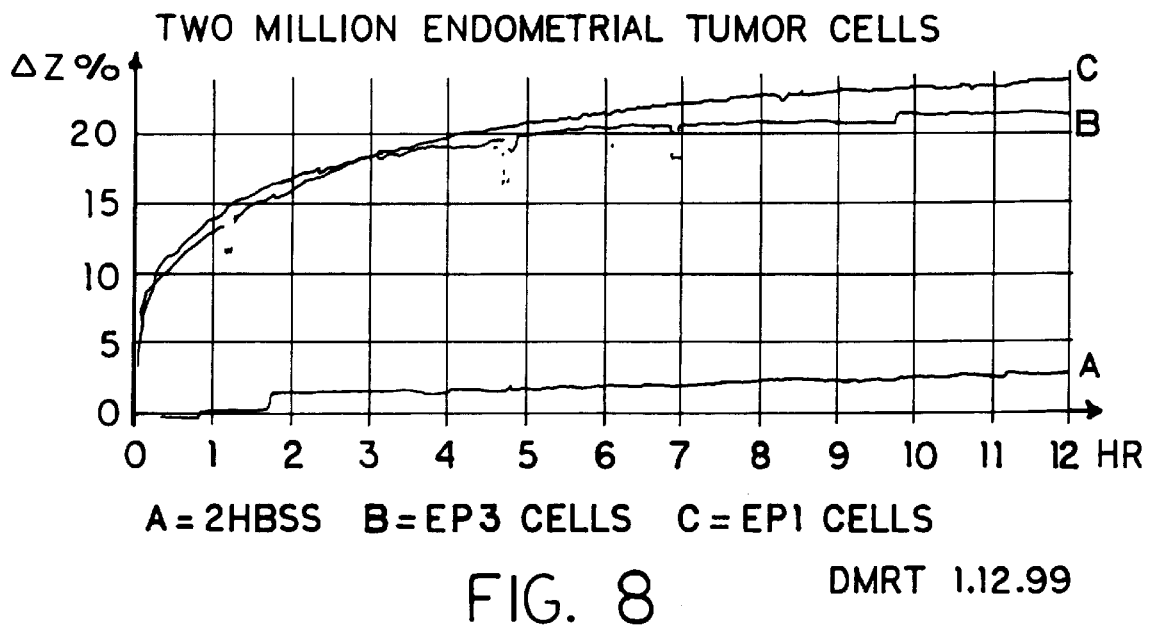
FIG. 8 DMRT 1.12.99
FIG. 9 DMRT 1.12.99
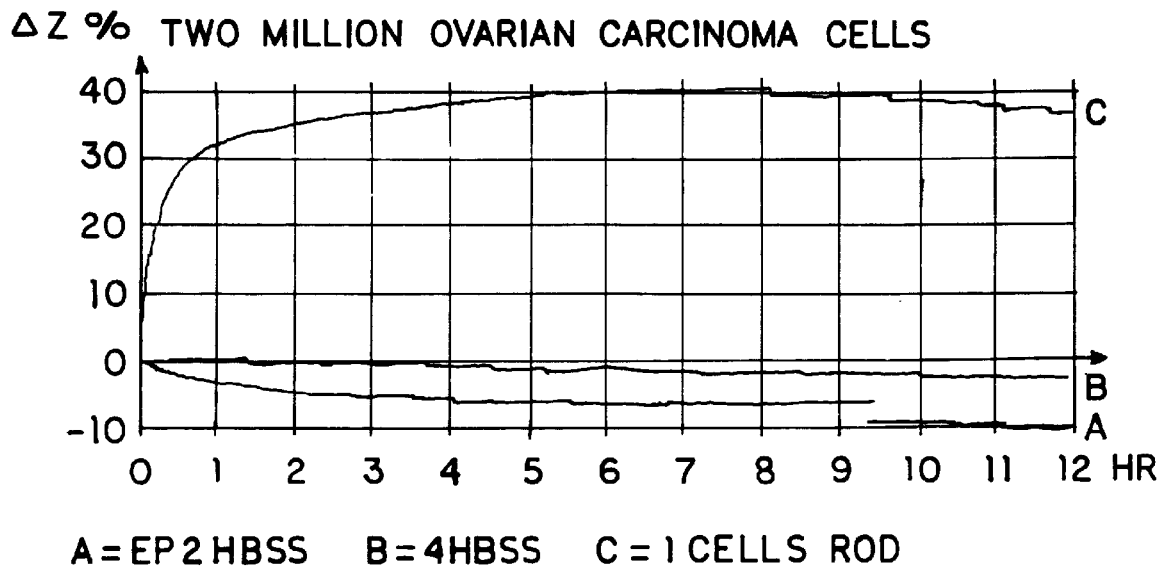

METHODS AND APPARATUS FOR MEASURING ELECTRICAL CHANGES IN NEOPLASMS AND FOODBORNE PATHOGENS IN A LIQUID MEDIUM

BACKGROUND OF THE INVENTION

1. Field of the Invention

The present invention relates generally to processes for food, more specifically to processes for meat, and particularly to processes for meat derived from aquatic environments.

2. General Background

Two broad categories of meat are recognized: meat derived from dry land environments and meat derived from an aquatic environment. Dry land derived meat generally, as a first step in processing, have the entrails removed. E-coli, which is abundant in mammalian intestines, is a potentially lethal pathogen in food and care is required in assuring that the fecal material in the intestines of mammals is removed.

The first category is further considered in two classes: poultry and other types. Poultry is considered to be inclusive of chicken, turkey, duck and other types encompassed by USDA regulation as poultry. Other types of dry land derived meat considered to be inclusive of beef, veal pork, lamb, et cetera. USDA regulations for poultry processing specify that chicken carcasses be cooled to below forty degrees Fahrenheit within four hours of slaughter and that at least two quarts of water flow per carcass be used in chilling. Chilled water tanks are hence conventionally utilized in processing chickens in the United States and a similar procedure is applicable to other types of dry land derived meat.

Meat derived from an aquatic environment similarly considered in two broad categories, fish and shellfish. Shellfish is inclusive of mollusks and crustaceans which are filter feeders and which, by definition pass a relatively large amount of water through a structure acting as a filter for food and excrete indigestible material which is digested along with the food so obtained. The contamination of meat, generally, especially meat derived from aquatic environments, and most particularly shellfish, has become recognized as a problem of tremendous importance in relatively recent years. Shellfish are filter feeders and therefore perhaps logically quite sensitive to and readily affected adversely by contamination of the pertinent aquatic environment.

The loss of substantial shellfish harvest in the Gulf of Mexico to the contamination of those waters by the effluent carried largely by the Mississippi River is an example of the loss of shellfish and more generally of meat derived from aquatic environments due to contamination. The ingestion of contaminated shellfish is further known as the cause of hundreds on incident of illness annually in the United States. The main concern is recognized as bacteriological contamination by foodborne pathogens including pseudomonas, vibrio, salmonella, and listeria which are also known as the spoilage microflora.

The particular problem concerned, moreover, is considered to have several components. The first component, contamination of aquatic environment is regarded as a given condition which varies considerably by geography. The second component is minimization of the shellfish contamination consequent the initial contamination. Irradiation is one known means of reducing spoilage microfloral populations but irradiation is also known to be destructive of food stuffs generally and shellfish particularly. The third component is determination of the level of contamination present in the shellfish at a given time, especially before and after processing as suggested in this invention. Accurate and timely determination of contamination levels would facilitate minimization of irradiation utilized and the adverse effects to the shellfish caused by the same.

3. Discussion of the Prior Art

The large scale irradiation of meat derived from aquatic environments is not presently permitted in the United States. The determination of pathogen level from a sample of meat is conventionally conducted with use of cultures grown in an appropriate medium, typically a gel, such as agar which undergoes a period of incubation in order to develop colonies which may be accurately measured. The length of time required for accurate determination of a pathogen level varies according, mainly, to the growth rate of the pathogen. This is typically on the order of 48–72 hours unless optical devices are employed which measure the opacity of a fluid sample as opposed to the colony growth in a petri dish. An accurate indication of pathogen level may be achieved, depending upon the pathogen, in six to twelve hours with use of optical opacity measuring devices.

U.S. Pat. Nos. 3,594,115, 3,699,437, 3,781,659 and 4,140,649 are referenced along with Canada No. 561,924 and Japan No. 62-100241. The first two U.S. patents and the last two foreign patents were cited by the examiner in U.S. Pat. No. 5,482,726 issued to the present applicant. The other two patents referenced were both issued to Amiram Ur MD and relate to the detection of blood coagulation by the use of conductivity cells measuring electrical impedance through fluid samples therein. The technology described in these two patent issued to Dr. Ur is concerned with the testing of human blood samples, specifically the rate of blood coagulation, which rate is valued as an indicator in many medical queries.

In addition to the above cited patents, it is noted that the use of ultrasound has been mentioned in the known prior art as a means of providing agitation to a bath of sanitizing solution for treating carcasses. "The sanitizing solution is preferably aerated or agitated during use in the tank. The sanitizing solution may be agitated through the use of ultrasound, paddles, brushes or other physical means. Aeration may be by bubbling or by other physical means. Aeration may be by bubbling or by other methods well known in the Art" (U.S. Pat. No. 5,234,703, Col. 5, lines 58–62). It is noted that this disclosure is of a particular sanitizing solution used in a conventional manner in accordance with detailed USDA procedures, claim 1 of said patent reading:

"A method for treating an animal carcass to eradicate bacteria from the carcass comprising:

(a) contacting the carcass with an aqueous solution having an effective amount of a medium chain fatty acid and a sufficient amount of an acid to maintain said solution at an acid pH."

In summary of the prior art it is first noted that irradiation with cobalt$^{60}$ is known as a common practice in the control of bacteriological contamination of certain edible food including spices and grain and that irradiation is approved by the USDA for beef, poultry and pork. It is secondly noted that conventional practice in the determination of pathogen level in meat involves the use of incubated cultures optically measured and that a determination of the rate of blood coagulation using conductivity cells through which changes in electrical impedance of samples held therein is known in the medical field. Thirdly, it is noted that ultrasound has been mentioned in the pertinent prior art as a means of providing agitation to a bath of sanitizing solution for carcasses which is considered in the prior art to be functionally equivalent to the use of paddles or brushes. Fourthly, it is noted that DNA sequence analysis methods can be used to identify specific strains of contaminants.

Statement of Need

Because contamination of meat is a serious problem, resulting in the loss of significant amounts of otherwise available harvest of the same and the illness of many people annually in the United States and because irradiation is known to be useful in destroying bacteriological contamination, there is considered a need for a method of ensuring an uncontaminated condition of meat, particularly meat derived from aquatic environments which is not excessively destructive of the meat, further preferably including means for the amelioration of the effects of the contamination of said meat.

SUMMARY OF THE INVENTION

Objects of the Invention

The preeminent objective of the invention is the provision of a method by which the quality regarding both pathogen contamination level and integrity of meat products is ensured during processing.

An auxiliary object of the present invention is the reduction of pathogen contamination of shellfish (meat) by use of irradiation.

An ancillary object of the present invention is the minimization of the irradiation required for reduction of pathogen contamination of meat by utilizing rapid determination of pathogen contamination level in meat in association with irradiation.

A second ancillary object of the present invention is the minimization of the irradiation required for reduction of pathogen contamination by utilizing ultrasonic baths for microscopic exterior cleansing of meat in association with irradiation.

A third ancillary object of the present invention is to determine genetic variations of foodborne neoplasms and pathogens such as hepatitis A and the immunodeficiency viruses (HIV) by utilization of mutant genomic assays.

Principles Relating to the Present Invention

In obtainment of the above stated objects the following elements are considered to be fundamental: (a) rapid detection of pathogen levels and rapid confirmation of neoplasm presence (b) pathogen reduction in meat by means of irradiation; (c) minimization of the destruction of the integrity of meat associated with irradiation by means of rapid determination of a pathogen contamination level; (d) minimization of the destruction of the integrity of meat associated with irradiation by means of microscopic cleansing of meat exterior surfaces effected with utilization of an ultrasonic bath; (e) minimization of the destruction of the integrity of meat associated with irradiation by means of enhanced depuration of shellfish effected with utilization of an ultrasonic bath; and (f) determination of genomic variations for (pathogenic) strain identification. Many other particular considerations are associated with a practical method utilizing a combination of the above stated fundamental elements according to the type of meat addressed.

As mentioned earlier, processing of mammalian meat includes removal of fecal material as a first step. The intestines and fecal material of fish may also be removed as a first step in processing. This is not true for shellfish. Shrimp may be decapitated in order to remove the majority of pathogens thereby. Mollusks are simply thrown on ice. Because shellfish are filter feeders. However, a large amount of contamination typically found therein maybe purged by natural processes. Ultrasonic waves applied to a tank holding live shellfish accelerates the natural deputation process. Ultrasonic waves of sufficient energy intensity applied to a tank containing solid objects immersed in the fluid held therein will cause cavitation to impinge upon the exterior surfaces of the immersed objects. This use of ultrasound in a tank containing an aqueous medium may be applied to any type of meat in order to cleanse the exterior surface of the meat microscopically.

Removal of the fecal material and the use of ultrasound for both microscopic exterior cleansing of meat and enhanced depuration of live shellfish provide both comprised means of minimizing the contamination of meat during processing of the same. Further reduction of pathogen level by irradiation is recommended, particularly in association with methods of rapid detection of pathogen levels in order to minimize the irradiation utilized and the destruction of the integrity of the meat irradiated. Use of an electron beam generator is recommended as a cold source of irradiation which is opposed to a hot source such as cobalt$^{60}$.

The basic method for rapid detection of pathogen level is also applicable to detecting the presence of malignant tumors, i.e., neoplasms in animal tissue. The electrical impedance of a fluid sample of meat tissue is measured over time. The meat is no longer alive and normal cell division has ceased. Cell division by both pathogens and neoplasms, however, continues and is detectable using balanced circuitry having two arms each electrically connected to one of two electrodes disposed upon either end of a conductive cell. Two such cells are utilized wherein one cell acts as a reference and the other test cell. The reference may have a thin film of a specific inhibitor of the activity monitored in the sample placed in the cell. Alternatively, the reference sample may have a specific inhibitor placed in solution with the sample which is otherwise identical with the test sample.

When a known deoxyoligomer probe hybridizes a complementary DNA target and generates a mismatch, the specific cleavage at the mismatch by mismatch repari enzymes reveals the base of a mutation in the DNA target or a specific DNA sequence such as an infectious microorganism (Hsu et al 1998). For biological samples of genetic or infectious diseases, a direct detection of mismatch cleavage needs a sensitivity able to detect a few million or even a few target DNA molecules (Hsu et al 1992). Amplification of the mismatch cleavage at the probe has improved the detection of human immunodeficiency virus (HIV) target and mutated bacterial and human DNA sequences (Craig et al 1996).

The assay relies on the high mismatch specificity of mutant proteins. The estimated sensitivity of the assay currently is up to 1%. Thus, a single base change in genomic DNA from tumor cells that are present in only 1% of normal cell background can be detected by this method. Research suggest, mismatch repair enzymes have an amino binding site that forms the Schiff base of the deoxyribose in the target DNA substrate (Hsu et al 1998).

BRIEF DESCRIPTION OF THE DRAWINGS

FIG. 3 is a plain elevational view of an apparatus utilizing circuitry such as that represented in FIG. 1 in order to display the comparative electrical impedances over time between a reference and test cells both containing fluid samples from the same tissue source.

FIGS. 5–9 are graphical representations of the growth curves for various pathogens as measured using the comparison of electrical impedances between test cells as generated by an apparatus such as depicted in FIGS. 2 & 3 above.

DETAILED DESCRIPTION OF THE PREFERRED EMBODIMENT

Direct quantitative methods have been developed to measure sensitivities of drug resistant cell lines of bacteria, viruses and soft tissue neoplasms found on meat poultry carcasses and live shellfish. Using electrical measurements as indices of metabolic activity through quantitative sensitivity can be obtained in less than four hours of working time after biopsy of neoplasms from various sources. Single DNA base identification techniques can be used for positive strain identification. Changes in the electrical physical properties of the media i.e., impedance or conductance are measured as a quantitative indicia of metabolic activity, particularly cell division. The sensitivity of this method is such that the metabolic activity of only three hundred E-coli cells is ascertained within two hours and three thousand E-coli cells ascertained within twenty minutes. Other pathogen levels determined with this method include Staphloccus, Klebsiella, Serratia, Pseudomonas, Lactobacillus, Pediococcus, Acetobacter, Candia and Mycoplasma. The detection of single base mismatches by mutant enzymes has been used to identify separate strains of the human immunodeficiency virus (HIV). This method has also been used for the rapid detection and identification of neoplasms in soft tissue samples.

Figure 1:
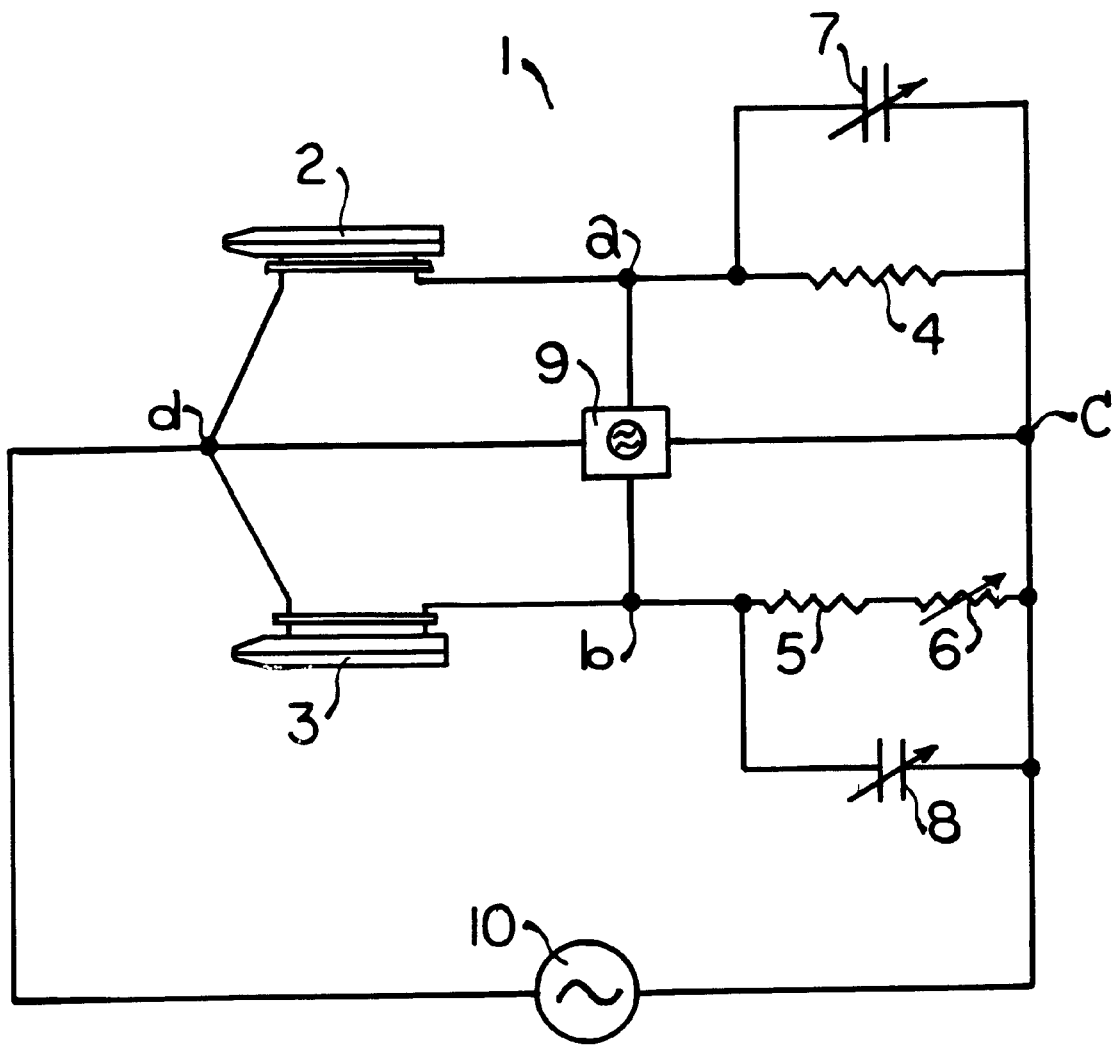
FIG. 1 is a schematic of a balanced bridge circuit (PRIOR ART) utilized for measuring the comparative electrical impedances over time between a reference and test cells both containing fluid samples from the same tissue source.
Figure 4A:
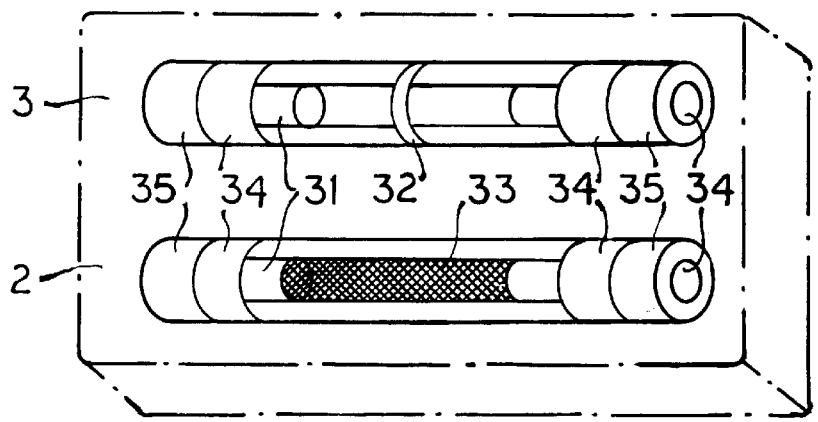
FIG. 4A (PRIOR ART) is a view of a conductivity cell in which samples of tissue are placed for measuring electrical impedances over time between the reference and test cells.

FIG. 1 depicts a balanced bridge circuit 1 appropriate for determining comparative metabolic activity between two samples taken from meat tissue. One sample is placed in a reference cell 2 in which the specific activity monitored is inhibited, either by a thin film 33 disposed upon the inner wall interior surface of the reference cell 2 as depicted in FIG. 4A or doping of the cell wall which is basically constructed from glass. This reference cell 2 comprises a third arm of the bridge which is connected in series with the fourth arm through a resistor 4 connected in parallel with a trimming capacitor 7 which is provided for balancing the reactance of the arm. An electrically and physically matched conductivity test cell 3 comprises the first arm of the bridge which is connected in series with a second arm comprised of a resistor 5 and a rheostat 6 connected in parallel with a trimming capacitor 8 for balancing the reactance arm. With the reactance of the second and fourth arms balanced by use of the trimming capacitors 7, 8 and the first and third arms, respectively, connected in series with the second and fourth arms, the impedance change to be monitored through the test cell 3 is purely resistive and the rheostat 6 may be adjusted to balance the bridge and the changes in impedance through the test cell 3 correspond directly to the inverse of the value of the rheostat 6 required for balancing.

The balanced bridge circuit 1 is supplied with a low voltage alternating current with a suggested frequency of about ten kilohertz derived, as shown in FIG. 1, from an oscillator 10. The double beam oscilloscope 9 displays the two signals derived from the two pairs of taps taken between points a and b and points c and d. The reactance of both signals are balanced with the use of the trimming capacitors 7, 8 which reduces the amplitude of each signal to pure resistance. Adjustment of the rheostat 6 brings the amplitude of the signals into balance and reading the rheostat 6 yields the difference in resistance through the test cell 3 compared with the resistance through the reference cell 2, as mentioned above.

Figure 4B:
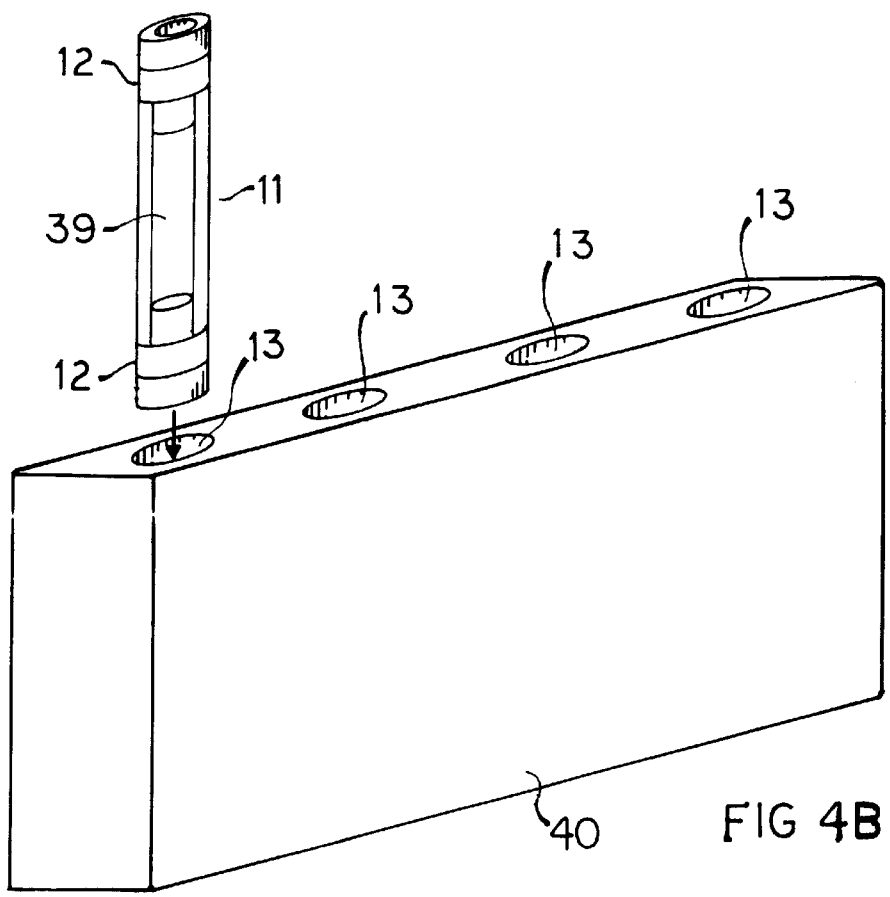
FIG. 4B is a perspective drawing of the improved conductivity cell.

It is not necessary, however, to use a pair of conductivity cells 2, 3 as shown in FIGS. 1 & 4A in a balanced bridge circuit 1 such as that shown in FIG. 1. A balanced bridge circuit 1 is necessary but a single test cell through which changes in impedance may be measured and compared with an equivalent impedance 37, obtained with repeated minimal value readings establishing benchmark data indicating healthy normal tissue, used in place of the reference cell. This approach is represented in FIGS. 2 & 4B wherein a single conductivity cell 11 having an electrode 12 at each end is contained in a chamber 13 which is maintained at a constant temperature with a heater 14 controlled by a thermistor 15 through a relay 16 and supplied with direct current through a full wave rectifier 17 supplied by a first transformer 19 which is supplied by a standard alternating current supply 29.

Two electrodes 12 are connected so that the conductivity cell 11 comprises an arm 20 of a balanced bridge 21 which is supplied with low voltage alternating current from a step down transformer 22 which is supplied from the first transformer 19 through a series connected capacitor and resistor 28 which set the frequency of the alternating current supplied to the bridge circuit 21 which is balanced with a capacitor coupled potentiometer 23. The bridge signal output 25 is read by a control computer 26 after passing through an amplification circuit 27 the gain of which is controlled by a second potentiometer 24.

Figure 2:
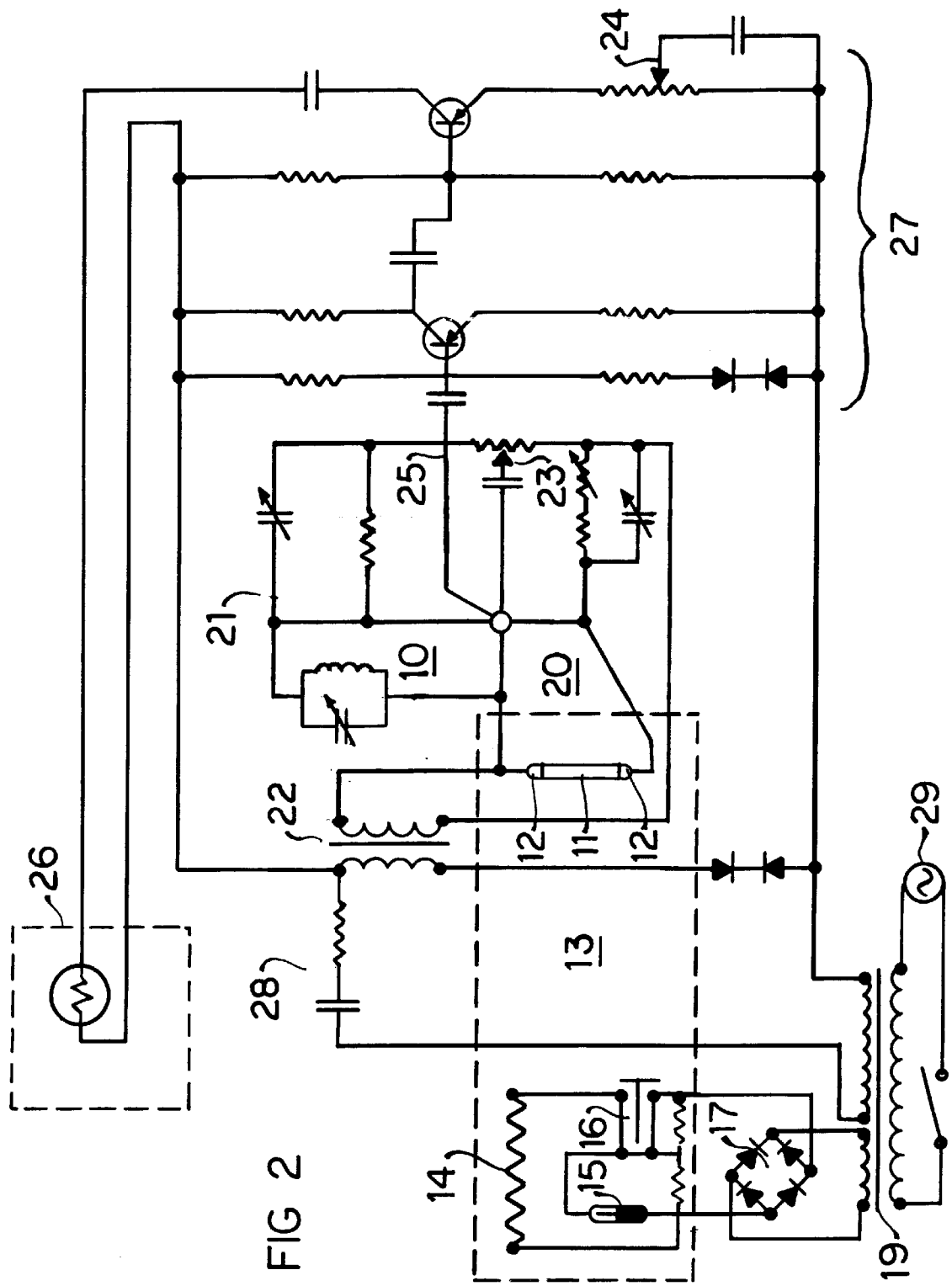
FIG. 2 is a schematic of the preferred circuitry utilized in an apparatus utilizing a balanced bridge circuit in order to display the comparative electrical impedances over time between a reference and test cells both containing fluid samples from the same tissue source.

The amplification circuit 27 depicted in FIG. 2 is of an ordinary two stage transistor type in which each transistor is of an ordinary common emitter type. Considerable amplification is utilized largely because the recorder 36, as more clearly seen in FIG. 3, is of the type through which a roll of paper is mechanically advanced and a needle 30, pivoted about an axis normal to the plane of the paper, oscillates in response to the amplified signal output 25 from the bridge circuit 21. If, instead of a mechanical recorder 36 a single or double beam oscilloscope 9 is used, little or no amplification is required. Other means of displaying the signal output 25 derived from the balanced bridge circuit 21 may also be utilized. A computer 26, or computer network 40, appropriately programmed, or connected with interface circuit, may be utilized for this purpose.

It is essential that a balanced bridge circuit 21 be utilized in order to provide the sensitivity required for measuring the changes in impedance through a conductivity cell 11 which result from biological cell metabolism. Pathogens, as mentioned earlier, continue to proliferate after the resident tissue has ceased metabolic functioning. Cell division is the primary component of metabolism detected by changes in impedance. Neoplasms, which have a higher rate of cell division than normal, healthy tissue, may be distinguished by a commensurately higher rate of change in impedance in a manner similar to pathogen proliferation. The reference for neoplasm detection is healthy tissue. A biopsy first of healthy tissue is tested to set a benchmark in the single conductivity cell 11 approach depicted in FIG. 2, followed by testing of the sample suspected to contain a neoplasm or carcinoma. 0.2 sigma indicates significant deviation.

Regardless of the approach using single, paired or other cell configuration, appropriate circuity utilizing a balanced bridge 21 to monitor metabolic activity yields a graphic display over time such as that depicted in FIGS. 5–9 wherein the growth curves of various species of Salmonella, E. coli, along with Listeria and Ovarian, Endometrial and Breast Cancers are shown. It is noted that with a known and fixed amount of current through a circuit the change in voltage is directly proportional to the change in resistance. Therefore the results displayed in FIG. 5 as change in voltage over time is the same as change in resistance over time which is derived from the balanced bridge circuit 1 depicted in FIG. 1.

It is also noted that the conductivity cells 2, 3, 11 utilized must possess certain physical characteristics. If a pair of cells 2, 3 are used simultaneously as depicted in FIGS. 1 & 4A, the two must be identical with regard to these physical characteristics. With reference to FIG. 4A it is seen that conductivity cells 2, 3 possess an electrode 34 and exterior insulation 35 proximate either end, that each cell 2, 3 consists of a cylinder of the same length, same outer diameter, and same inner diameter. All cells 2, 3 further possess an interior extension 31 of each electrode 34. Aside from being identical physically, particularly with regard to the volume contained therein and most particularly the distance between the interior extensions 31 of the electrodes 34, it is essential that each cell 2, 3 possess identical properties. The test cell 3 in this case, as depicted in FIG. 4A, possesses an exterior band 32 for identification. FIGS. 5–9 shows the resultant traces of exposing meat (tissue) samples to various amounts of anti-bacterial and anti-cancer drugs while suspended in liquid media.

Use of balanced bridge circuitry 1, 21 for the rapid determination of pathogen levels in meat or detection of neoplasm in tissue samples relies upon the difference in the rate of metabolism exhibited by these organisms in comparison with healthy meat tissue. Assuming use of electrically identical conductivity cells 11, use of a reference cell 2 simultaneously with a test cell 3 is not necessary. Reference or benchmark data may be established and used for interpretation of the measurements obtained in the changes in impedance over time of the test sample 39 of known volume, and a healthy or normal sample 39 of known volume can be run in order to calibrate or zero the measurement scale based upon the reference or benchmark data.

This is considered key to the present invention. With rapid determination of pathogen levels or the presence of neoplasm in meat samples other factors for assuring meat quality are readily implemented. A sufficient but minimal level of irradiation may be utilized which will preserve the integrity of the meat and reduce pathogen levels to desired, safe, levels. The effectiveness of the irradiation or, more particularly, of other measures taken to prevent or retard spoilage and ensure meat quality may be readily ascertained and the quality of the meat thus assured. The effectiveness of ultrasonic exterior cleansing and depuration of live shellfish in the reduction of pathogen contamination can be quantitatively measured. Sanitary conditions can be verified. Rapid pathogen level determination and neoplasm recognition is also considered valuable as an indicator of unwholesome meat and environmental contamination. Qualitative genetic analysis can be used to determine genomic strain variations using DNA target sequencing techniques. The element considered key to all these aspects is the provision of empirical, quantitative, and qualitative indicia of tissue quality.

I claim:

1. A system intended to provide empirical, quantitative, and qualitative indicia of pathogen levels, said system comprising:

means for passing alternating current of a known frequency and voltage through a test cell possessing two ends made of a dielectric material holding a biological tissue sample of known volume between two electrodes each spaced apart from each other a known distance, each electrode further being bonded to one of said two ends of said test cell;

means for passing said alternating current between said two electrodes of said test cell through a circuit including a bridge wherein said test cell holding said biological tissue sample effectively comprises one arm of said bridge, equivalent impedance another arm of said bridge, and changes in the impedance of the biological sample to said alternating current passing through said test cell disturbs the balancing of said bridge;

means for passing said alternating current through a circuit connected to said bridge which is capable of measuring changes in the impedance of the biological sample to said alternating current passing through said test cell as determined by an opposed impedance required in balancing said bridge disturbed by the changes in impedance of the biological tissue sample to said alternating current passing through said test cell.

2. An apparatus intended for use in the system of claim 1 for obtaining characteristic curves of biological fluids, said apparatus comprising:

a temperature controlled chamber and at least one conductivity cell in said chamber adapted to hold a biological fluid sample to be tested;

each said conductivity cell possessing two electrodes adapted to measure electrical impedance of the biological fluid sample held therein;

an electrical measuring circuit including a bridge adapted for operating with alternating current, said bridge including a plurality of arms, said electrodes of each said conductivity cell being connected to one of said arms, the bridge being adapted to become unbalanced by variation of the impedance to alternating current passed through each said fluid sample and electrically coupling two electrodes;

whereby an output signal taken from said bridge having the same frequency as said alternating current possesses an amplitude according to the impedance of one fluid sample through which said electrodes are electrically coupled and a change in said amplitude reflects the number of ions produced in the conductivity cell;

whereby registering means connected to said measuring circuit provides a transmittable signal to a computer for analysis.

3. Apparatus as claimed in claim 2 including an AC generator supplying line voltage to said registering means possessing a frequency greater than that of said alternating current passed through each said conductivity cell.

4. Apparatus as claimed in claim 2 wherein the AC generator is a solid state oscillator.

5. Apparatus as claimed in claim 2 having at least two physically and electrically matched conductivity cells each electrically joined to said electrical measuring circuit.

6. The apparatus of claim 5 wherein at least one of said conductivity cells is utilized as a reference for measuring impedance changes in at least one other cell and possesses means marking the reference cell to identify the same.

7. The apparatus claimed in claim 5 including a cassette holder for at least four matched conductivity cells.

8. The apparatus of claim 2 further possessing an interface circuit connecting a plurality of computers together to form a network of computers.

9. The system of claim 1 further possessing temperature control means operatively associated with said test cell.

10. The apparatus of claim 5 wherein said reference cell contains a pathogen growth inhibiting substance.

* * * * *